United States Patent [19]

Hagarty

[11] Patent Number: 6,028,117
[45] Date of Patent: Feb. 22, 2000

[54] MICROEMULSION INSECT CONTROL COMPOSITIONS

[75] Inventor: John D. Hagarty, Racine, Wis.

[73] Assignee: S. C. Johnson & Son, Inc., Racine, Wis.

[21] Appl. No.: 08/768,547

[22] Filed: Dec. 18, 1996

[51] Int. Cl.$^7$ .......................... A01N 27/00; A01N 29/00; A01N 25/04; A01N 25/06

[52] U.S. Cl. .......................... 514/762; 514/715; 514/717; 514/722; 514/723; 514/724; 514/729; 514/730; 514/738; 514/739; 514/743; 514/757; 514/763; 514/764; 514/765; 514/766; 514/767; 514/768; 514/789; 514/937; 514/938; 514/939; 514/943; 424/43; 424/45; 424/405

[58] Field of Search .......................... 514/762, 937, 514/938, 763–768, 724, 729, 730, 738, 739, 743, 715, 757, 717, 722, 723, 789, 939, 943; 424/45, 405, 43

[56] References Cited

U.S. PATENT DOCUMENTS

| | | | |
|---|---|---|---|
| 4,146,499 | 3/1979 | Rosano | 252/186.32 |
| 4,472,291 | 9/1984 | Rosano | 252/186.28 |
| 4,889,710 | 12/1989 | Hagarty | 424/84 |
| 4,923,698 | 5/1990 | Rodero | 424/405 |
| 5,037,653 | 8/1991 | Dawson | 424/405 |
| 5,078,782 | 1/1992 | Nielsen et al. | 514/937 |
| 5,093,124 | 3/1992 | Kulenkampff | 424/406 |
| 5,145,604 | 9/1992 | Neumiller | 252/312 |
| 5,178,871 | 1/1993 | Thill | 424/405 |
| 5,254,344 | 10/1993 | Dookhith et al. | 424/405 |
| 5,385,948 | 1/1995 | Chaudhuri et al. | 514/788 |
| 5,389,688 | 2/1995 | Narayanan | 514/788 |
| 5,489,433 | 2/1996 | Aboud | 424/405 |
| 5,603,942 | 2/1997 | Narayanan et al. | 424/405 |

FOREIGN PATENT DOCUMENTS

| | | |
|---|---|---|
| 160182 | 11/1985 | European Pat. Off. . |
| 360883 | 4/1990 | European Pat. Off. . |
| 392127 | 10/1990 | European Pat. Off. . |
| 620271 | 10/1994 | European Pat. Off. . |
| 0 677 579 A1 | 10/1995 | European Pat. Off. . |
| 86/22686 | 10/1996 | WIPO . |
| 96/36225 | 11/1996 | WIPO . |

OTHER PUBLICATIONS

1975 Farm Chemicals Handbook, Meister Publishing Co., Ohio, 1975, p. D156.

King, W.V., Chemicals Evaluated as Insecticides and Repellents at Orlando, FIA, U.S. Dept. of Agriculture, Agriculture Handbook No. 69, 1954, pp. 1–17, 188, and 232.

*Primary Examiner*—John Pak

[57] ABSTRACT

Disclosed herein are microemulsion insecticides that do not contain conventional actives. The microemulsion form permits insects to be killed by an oil/surfactant combination.

9 Claims, No Drawings

MICROEMULSION INSECT CONTROL COMPOSITIONS

BACKGROUND OF THE INVENTION

The present invention relates to microemulsions capable of killing insects without the use of conventional insecticides. It is particularly useful in killing crawling insects that have hard, waxy exoskeletons.

Hydrocarbon solvents assist in insect knock-down. Unfortunately, many hydrocarbons are flammable and as a result conventional insect control agents are sometimes delivered via oil/water type emulsions. See e.g. U.S. Pat. No. 5,145,604. The disclosure of this patent, and of all other publications referred to herein, are incorporated by reference as if fully set forth herein.

However, many prior art oil/water emulsions are unstable. The user must shake the container shortly before use to recreate the emulsion on a temporary basis. The art therefore developed much more stable microemulsions containing water, hydrocarbon, conventional insecticide, and one or more emulsifiers. See e.g. U.S. Pat. No. 5,037,653. For purposes of this application a "microemulsion" is a transparent, stable dispersion of oil and water where the dispersed phase consists mostly of small droplets with diameters between 10 and 100 millimicrons.

However, because such prior art insecticides contain conventional insecticidal actives, they are subject to stringent regulatory control, have a relatively high cost, have limitations on their use (e.g. not too close to food), and are sometimes perceived by the public as environmentally undesirable.

Some have tried applying surfactant solutions directly to insects as a more natural insecticide approach. See e.g. U.S. Pat. No. 5,489,433. However, this approach is not very effective against hard body insects such as cockroaches.

Thus, a need exists for improved, environmentally safe insect control compositions.

BRIEF SUMMARY OF THE INVENTION

In one aspect, the invention provides a microemulsion. Total hydrocarbon solvent in the microemulsion is above 20% and below 60% (by weight). If a hydrocarbon propellant is used it forms part of the hydrocarbon solvent, and the portion of the hydrocarbon solvent apart from the propellant is preferably between 15% and 35% (by weight) of the overall microemulsion. Preferably, the microemulsion is capable of causing "knockdown" of at least 80% of a German cockroach population in the "Standard Test" described below, in one minute or less.

Surfactant is between 1% and 20% by weight of the microemulsion, and at least 10% by weight of the microemulsion is water (preferably above 30%). Importantly, there is essentially no "Conventional Insecticidal Active", as that term is defined below.

The above microemulsions are preferably delivered in aerosol form. I prefer to have 5% or more (e.g. 10–25%) by weight of the microemulsion be a hydrocarbon propellant dispersed in the microemulsion.

A wide variety of gaseous hydrocarbons can be used for this purpose. They typically liquify under the pressure conditions of an aerosol can and become part of the hydrocarbon solvent. For example, the propellant can be dimethylether, difluoroethane, propane, butane, isobutane and mixtures thereof. A particularly preferred propellant B-70 from Phillips Petroleum, which is a propane/n-butane/isobutane, 55/27/18 (mole %) mixture. Another is A-70 from Phillips Petroleum, a 45/55 (mole %) propane/isobutane mixture. For purposes of this patent, a "hydrocarbon" only has carbon and hydrogen.

A wide variety of other hydrocarbon solvents can be used (apart from the propellant). Preferably, these non-propellant hydrocarbons have between 6 and 20 carbons. Examples include hexane, benzene, toluene, xylene, mineral spirits, mineral oil, d-limonene, heavy aromatic naphtha, kerosene, paraffins, and other alkanes and alkenes. Particularly preferred hydrocarbons are EXXSOL brand hydrocarbons from Exxon/Esso. These are typically mixtures of hydrocarbons below $C_{20}$ (alkanes, alkenes). Especially preferred are EXXSOL D-95 and EXXSOL D-60.

Surfactants can be cationic, anionic, amphoteric and nonionic surfactants. However, we prefer to use a mixture of an anionic surfactant and a nonionic surfactant. See generally EP677,579.

Especially preferred is an essentially equal mix of isopropylamine sulfonate (Calimulse PRS; Pilot Chemical) and a tristyrylphenol, such as tristyrylphenol ethoxylate (Soprophor BSU; Rhone Poulenc). Other suitable nonionic surfactants are Soprophors 4D 384 and FL, and polyethoxylates derived from primary and secondary aliphatic alcohols having from 8 to 24 carbons atoms in the alcohol alkyl chain. In addition, part or all of the ethylene oxide may be replaced by propylene oxide.

Still other suitable nonionic detergents are polyoxyalkylene alkyl phenols; polyalkylene esters of the higher organic acids having 8 or more carbon atoms in the acid hydrophobe and 10 or more moles of ethylene oxide as a hydrophilic group; polyalkylene alkyl amines whose hydrophobic group is from a primary, secondary or tertiary amine and whose ethylene oxide content is sufficiently high to impart both water solubility and nonionic characteristics, usually derived from fatty acids with 8 or more carbons; polyalkylene alkyl amides having a hydrophobic group derived from an amide of a fatty acid or ester; fatty acid esters of glycols, polyalkylene oxide block copolymer and the like.

Representative of the suitable anionic surfactants alkyl aryl sulfonates of 6 to 20 carbons atoms in the alkyl group; $C_{10}$–$C_{22}$ fatty acid soaps; $C_{10}$–$C_{22}$ fatty sulfates; $C_{10}$–$C_{22}$ alkyl sulfonates, including the alkali metal salts of the higher alkyl and linear paraffin sulfonic acids and salts thereof; alkali metal dialkyl sulfosuccinates, ethoxylated alcohol sulfates, phosphate esters, taurates, and the like. See also U.S. Pat. No. 5,037,653 for other surfactants.

For purposes of this application, "Conventional Insecticidal Active" shall mean insecticidally active synthetic pyrethroids (e.g. cypermethrin, cyfluthrin, lambda-cyhalothrin, allethrin forte, phenathrin, d-phenathrin, tetramethrin, resmethrin, esbiothrin, allethrin, permethrin, d-trans allethrin and kadethrin), natural pyrethrum (e.g. pyrethrins), organophosphates (e.g. chlorpyrifos), carbamates (e.g. Baygon), and chlorinated hydrocarbons (e.g. methoxychlor), and heterocyclics (e.g. phenyl pyrroles).

In order to achieve acceptable performance at relatively low emulsifier levels, co-solvent alcohols can also be used. Preferably, a mixture of primary organic alcohols are added. One can be a primary aliphatic alcohol having a carbon content of between 3 and 12 carbons (e.g. 1-octanol (Alfol 8), 1-hexanol, 1-pentanol, or 1-butanol). The other can be a non-aromatic ether alcohol having less than 20 carbons (e.g. diethylene glycol monohexyl ether (hexyl carbitol), diethylene glycol mono-butyl ether, or propylene glycol monobutyl ether). Also, certain glycols such as hexylene glycol, triethylene glycol, or 1,4-butanediol can be added.

When the microemulsion contains a gaseous propellant and is pressurized, the microemulsion can be sprayed from an aerosol can. As an alternative, a pump spray container (without propellant) can be used. The spray is preferably projected directly at a crawling insect. Because the spray is a microemulsion, it is very stable. Thus, if the aerosol can has been shaken at the factory, a consumer need not shake the can before use.

The hydrocarbon helps the emulsifier penetrate the insect's outer shell. The emulsifier is then able to knock-down and thus kill more effectively. The particle size due to the existence of the microemulsion is particularly important in assisting in shell penetration.

Because the levels of hydrocarbons are high, the microemulsion has excellent knock-down characteristics. Moreover, notwithstanding the high hydrocarbon levels flammability is acceptably low.

Deionized water is preferred (e.g. 20–50% by weight). Also, other standard additives can be added such as corrosion inhibitors and fragrances.

A preferred pH range for the microemulsion is between pH 6 and pH 8. Too low a pH can cause can corrosion and may also adversely affect surfaces that are sprayed. Too high a pH may adversely affect surfaces that are sprayed or cause consumer concern.

Insects that can be killed by these microemulsions include cockroaches (e.g. German, American), ants, silverfish, and other crawling insects.

The objects of the present invention include providing an insecticide:

(a) which does not have a Conventional Insecticidal Active;

(b) which does not require shaking by a consumer prior to use;

(c) which is effective against crawling insects such as cockroaches;

(d) which is relatively inexpensive to produce;

(e) which is suitable to be delivered in an aerosol form; and (f) which is suitable for use even near areas where food is present.

These and still other objects and advantages of the present invention (e.g. methods for using such microemulsions) will be apparent from the description which follows. The following description is merely of the preferred embodiments. Thus, the claims should be looked to in order to understand the full scope of the invention.

DETAILED DESCRIPTION

Experimental Preparations

| Ingredient (by weight) | A (Microemulsion) | B (Micro - emulsion) | C (Macroemulsion) |
|---|---|---|---|
| hydrocarbon solvent | 25% Exxsol D-95 | 25% Exxsol D-95 | 25% Exxsol D-95 |
| anionic surfactant | 2% Calimulse PRS | — | 2% Calimulse PRS |
| cationic surfactant | — | 3% Variquat K-300 | — |
| nonionic surfactant | 2% Soprophor BSU | 2% Soprophor BSU | 2% Soprophor BSU |
| co-solvent | 8% Hexyl Carbitol | 8% Hexyl Carbitol | 8% Hexyl Carbitol |
| co-solvent | 1.4% 1-octanol | 1.2% 1-octanol | 1% 1-octanol |
| propellant | 18% B-70 | — | 18% B-70 |
| deionized water | 43.20% | 60.8% | 43.55% |
| fragrance | .15% | — | .15% |
| corrosion inhibitor | .25% Elfugin AKT | — | .25% Elfugin AKT |

Percentages are weight percentages.

Standard Test On Crawling Insects

To test the effectiveness of compounds A–C (A and B being compounds of the present invention; C being a macroemulsion) we ran direct spray knock-down tests. In one set of experiments (the "Standard Test"), seven week old adult male German cockroaches were transferred into clean greased Lucite rings (5 cm height×10 cm diameter) with an aluminum screen (6×7 mesh/cm) attached to the bottom of the ring. Cockroach testing containers (each containing ten roaches) were placed in a Water's Spray Tower and exposed to a targeted discharge aimed from above at a distance of 46 cm over 0.5 seconds. The Standard Test uses 1.5 g of the insecticide. As noted below, we also tried other amounts.

Immediately after each exposure/discharge the cockroaches were transferred to a clean greased glass battery jar for the selected observation periods. A knockdown is deemed achieved for purposes of this patent once the roach flips over on its back (regardless of leg or antennae movement). This is because once such roaches flip on their back in these tests they typically do not recover.

| Mean % Knockdown Vs. Time In Seconds (s) | | | | | | | | | |
|---|---|---|---|---|---|---|---|---|---|
| Sample | g/rep | 15s | 30s | 45s | 60s | 75s | 90s | 105s | 120s |
| C | 2.04 | 68 | 63 | 66 | 72 | 79 | 83 | 89 | 92 |
| A | 1.46 | 65 | 82 | 89 | 95 | 99 | 100 | 100 | 100 |
| Control | N/A | No Treatment | | | | | | | 0 |

Similar tests on other preferred formulations were conducted. It should be appreciated that the above description merely relates to several preferred forms of the invention. Other forms are also possible. For example, we have used other hydrocarbons such as d-limonene in our microemulsions.

INDUSTRIAL APPLICABILITY

The present invention provides environmentally friendly insecticides. It should be particularly useful in kitchen environments or as a house plant spray.

I claim:

1. A method of causing knockdown of a crawling insect, comprising:

applying an effective amount of a microemulsion to an exterior surface of a crawling insect and thereby causing it to flip over on its back;

wherein the microemulsion comprises:
hydrocarbon solvent which is above 20% by weight, and below 60% by weight, of the microemulsion;
surfactant which is between 1% by weight and 20% by weight of the microemulsion; and
at least 10% by weight water;
wherein the microemulsion contains essentially none of any compound selected from the group consisting of insecticidally active synthetic pyrethroids, natural pyrethrum, insecticidally active organophosphates, insecticidally active carbamates, insecticidally active chlorinated hydrocarbons, and insecticidally active heterocyclics.

2. The method of claim 1, wherein there is less than 6% by weight surfactant.

3. The method of claim 1, wherein at least 10% by weight of the microemulsion is a hydrocarbon propellant and there is less than 35% by weight of the microemulsion which is a hydrocarbon solvent apart from the propellant.

4. The method of claim 3, wherein the propellant is selected from the group consisting of dimethylether, difluoroethane, propane, butane, and mixtures thereof.

5. The method of claim 1, wherein the surfactant comprises an anionic surfactant and a nonionic surfactant.

6. The method of claim 1, wherein said microemulsion further comprises a co-solvent which is an organic alcohol.

7. The method of claim 6, wherein the organic alcohol comprises:
a primary alcohol having between 3 and 12 carbons; and
an ether alcohol having less than 20 carbons.

8. The method of claim 7, wherein the primary alcohol is 1-octanol and the ether alcohol is diethylene glycol monohexyl ether.

9. The method of claim 1, wherein the insect is selected from the group consisting of cockroaches, ants, earwigs, and silverfish.

* * * * *